(12) United States Patent
Jenkins et al.

(10) Patent No.: US 7,982,769 B2
(45) Date of Patent: *Jul. 19, 2011

(54) APPARATUS AND METHOD FOR COMPUTERIZED MULTI-MEDIA DATA ORGANIZATION AND TRANSMISSION

(75) Inventors: Deborah L. Jenkins, Fort Worth, TX (US); William Rex Akers, Colleyville, TX (US)

(73) Assignee: William Rex Akers, Fort Worth, TX (US)

( * ) Notice: Subject to any disclaimer, the term of this patent is extended or adjusted under 35 U.S.C. 154(b) by 665 days.

This patent is subject to a terminal disclaimer.

(21) Appl. No.: 10/366,179

(22) Filed: Feb. 13, 2003

(65) Prior Publication Data
US 2004/0017474 A1 Jan. 29, 2004

Related U.S. Application Data

(63) Continuation of application No. 09/170,509, filed on Oct. 13, 1998, now Pat. No. 6,597,392.

(60) Provisional application No. 60/061,761, filed on Oct. 14, 1997.

(51) Int. Cl.
| | |
|---|---|
| H04N 5/225 | (2006.01) |
| H04N 5/232 | (2006.01) |
| H04N 5/76 | (2006.01) |
| H04N 5/222 | (2006.01) |
| H04N 7/00 | (2011.01) |
| G06Q 10/00 | (2006.01) |
| A61B 5/00 | (2006.01) |

(52) U.S. Cl. ............... 348/207.1; 348/211.8; 348/231.5; 348/552; 348/333.02; 705/2; 600/301

(58) Field of Classification Search ............... 348/207.1, 348/211.99, 211.8, 211.9, 231.2, 231.5, 333.02, 348/552; 600/301; 705/3
See application file for complete search history.

(56) References Cited

U.S. PATENT DOCUMENTS
5,072,383 A 12/1991 Brimm et al.
(Continued)

FOREIGN PATENT DOCUMENTS
WO  WO 00/16222 A1  3/2000

OTHER PUBLICATIONS

Gomez, E. J. et al: "A Broadband Multimedia Collaborative System for Advanced Teleradiology and Medical Imaging Diagnosis"; IEEE Transactions on Information Technology in Biomedicine, IEEE Service Center, Los Alamitos, CA, USA, vol. 2, No. 3, Sep. 1998, pp. 146-155; XP-000831159.

(Continued)

*Primary Examiner* — Nhan T Tran
(74) *Attorney, Agent, or Firm* — Carr LLP

(57) ABSTRACT

Accordingly, the present invention provides an apparatus for multi-media data organization and transmission. The apparatus has a computer having a microprocessor, a memory storage, a display for providing information to a user, and an input device. An image-recording device is electrically-coupled to the computer for capturing images for storage in the memory storage of the computer. A database, which has a structure defined in the memory storage, receives and stores a plurality of information relating to an event. A program, being executable by the computer, provides a graphical user interface on the display. The program has an imaging module with document and image capture filing and scanning functions. The graphical user interface receives an input from the input device and from the image-recording device. In a further aspect of the invention, the program has a communications module for transmission of the plurality of information relating to the event to a remote location.

64 Claims, 5 Drawing Sheets

U.S. PATENT DOCUMENTS

| | | | |
|---|---|---|---|
| 5,262,944 | A | 11/1993 | Weisner et al. |
| 5,553,609 | A | 9/1996 | Chen et al. |
| 5,592,664 | A | 1/1997 | Starkey |
| 5,597,995 | A | 1/1997 | Williams et al. |
| 5,810,747 | A * | 9/1998 | Brudny et al. ............... 600/300 |
| 5,832,449 | A | 11/1998 | Cunningham |
| 5,842,175 | A | 11/1998 | Andros et al. |
| 5,845,255 | A | 12/1998 | Mayaud |
| 5,867,821 | A | 2/1999 | Ballantyne et al. |
| 5,899,998 | A | 5/1999 | McGaulkey et al. |
| 5,903,889 | A | 5/1999 | De La Huerga et al. |
| 5,907,493 | A | 5/1999 | Boyer et al. |
| 5,924,074 | A | 7/1999 | Evans |
| 5,950,630 | A | 9/1999 | Portwood et al. |
| 5,987,519 | A | 11/1999 | Peifer |
| 6,006,191 | A | 12/1999 | DiRenzo |
| 6,021,393 | A | 2/2000 | Honda et al. |
| 6,031,572 | A | 2/2000 | Christopoulos |
| 6,031,929 | A | 2/2000 | Maitz et al. |
| 6,035,323 | A | 3/2000 | Narayen et al. |
| 6,038,465 | A | 3/2000 | Melton, Jr. |
| 6,047,259 | A | 4/2000 | Campbell et al. |
| 6,055,506 | A | 4/2000 | Frasca, Jr. |
| 6,055,507 | A | 4/2000 | Cunningham |
| 6,067,524 | A | 5/2000 | Byerly et al. |
| 6,125,350 | A | 9/2000 | Dirbas |
| 6,131,090 | A | 10/2000 | Basso, Jr. et al. |
| 6,157,935 | A * | 12/2000 | Tran et al. .................... 715/202 |
| 6,202,923 | B1 | 3/2001 | Boyer et al. |
| 6,219,587 | B1 | 4/2001 | Ahlin et al. |
| 6,234,964 | B1 * | 5/2001 | Iliff .............................. 600/300 |
| 6,263,330 | B1 | 7/2001 | Bessette |
| 6,272,470 | B1 | 8/2001 | Teshima |
| 6,305,377 | B1 * | 10/2001 | Portwood et al. ............. 128/897 |
| 6,370,841 | B1 | 4/2002 | Chudy et al. |
| 6,597,392 | B1 * | 7/2003 | Jenkins et al. ............. 348/207.1 |
| 7,027,872 | B2 | 4/2006 | Thompson |
| 7,039,810 | B1 | 5/2006 | Nichols |
| 7,249,036 | B2 * | 7/2007 | Bayne .............................. 705/2 |
| 7,251,610 | B2 | 7/2007 | Alban |
| 2002/0169637 | A1 | 11/2002 | Akers et al. |

OTHER PUBLICATIONS

Gomez, E.J. et al: "Optimisation and Evaluation of an Asynchronous Transfer Mode Teleradiology Co-operative System: the Experience of EMERALD and the BONAPARTE Projects"; Computer Methods and Programs in Biomedicine, Elsevier, Ireland, vol. 64, No. 3, Mar. 2001, pp. 201-214; XP-002389681.
European Patent Office: Supplementary European Search Report; EP Application No. 02_74_7825; Munich DE, Aug. 8, 2006.
Search Report for PCT/US02/14682 Dated Dec. 27, 2002 in related PCT filing of U.S. Appl. No. 09/851,745.
U.S. Appl. No. 09/170,509; Office Action; Jun. 19, 2002.
U.S. Appl. No. 09/170,509; Response to Office Action; Sep. 17, 2002.
U.S. Appl. No. 09/170,509; Notice of Allowance/Notice of Allowability; Dec. 3, 2002.
U.S. Appl. No. 09/851,745; Petition and IDS; Oct. 9, 2001.
U.S. Appl. No. 09/851,745; Decision on Petition; Dec. 27, 2001.
U.S. Appl. No. 09/851,745; Petition; Jan. 17, 2002.
U.S. Appl. No. 09/851,745; Decision on Petition; Jan. 18, 2002.
U.S. Appl. No. 09/851,745; Office Action; Sep. 12, 2002.
U.S. Appl. No. 09/851,745; Response; Oct. 9, 2002.
U.S. Appl. No. 09/851,745; Final Office Action; Jan. 2, 2003.
U.S. Appl. No. 09/851,745; Examiner's Interview Summary; Jan. 21, 2003.
U.S. Appl. No. 09/851,745; Response; Mar. 11, 2003.
U.S. Appl. No. 09/851,745; Advisory Action; Mar. 21, 2003.
U.S. Appl. No. 09/851,745; Appeal Brief; Jul. 11, 2003.
U.S. Appl. No. 09/851,745; Examiner's Answer; Mar. 9, 2004.
U.S. Appl. No. 09/851,745; Reply Brief; May 13, 2004.
U.S. Appl. No. 09/851,745; Order Returning Undocketed Appeal to Examiner; Aug. 23, 2005.
U.S. Appl. No. 09/851,745; Second Examiner's Answer; Mar. 7, 2006.
U.S. Appl. No. 09/851,745; Final Office Action; Jan. 9, 2007.
U.S. Appl. No. 09/851,745; Office Action May 22, 2007.
U.S. Appl. No. 09/851,745; Response; Aug. 22, 2007.
U.S. Appl. No. 09/851,745; Final Office Action Nov. 19, 2007.
U.S. Appl. No. 09/851,745; Response; Apr. 21, 2008.
U.S. Appl. No. 09/851,745; Office Action; Jul. 24, 2008.
U.S. Appl. No. 09/851,745; Response; Nov. 24, 2008.
U.S. Appl. No. 09/851,745; Final Office Action; Mar. 4, 2009.
U.S. Appl. No. 10/369,843; Petition; Jul. 14, 2003.
U.S. Appl. No. 10/369,843; Decision on Petition; Jul. 28, 2003.
U.S. Appl. No. 10/369,843; Petition; Sep. 22, 2003.
U.S. Appl. No. 10/369,843; Decision on Petition; Sep. 30, 2003.
U.S. Appl. No. 10/369,843; Office Action; Dec. 14, 2006.
U.S. Appl. No. 10/369,843; Response; Apr. 16, 2007.
U.S. Appl. No. 10/369,843; Final Office Action; Jul. 2, 2007.
U.S. Appl. No. 10/369,843; Response; Jan. 2, 2008.
U.S. Appl. No. 10/369,843; Notice of Allowance; Jul. 21, 2008.
U.S. Appl. No. 10/369,843; Amendment Submitted with Request for Continued Examination; Oct. 21, 2008.
U.S. Appl. No. 10/369,843; Notice of Allowance; Nov. 21, 2008.
U.S. Appl. No. 10/369,843; Information Disclosure Statement Submitted with Request for Continued Examination; Feb. 23, 2009.
U.S. Appl. No. 10/369,843; Notice of Allowance; Mar. 2, 2009.
U.S. Appl. No. 10/369,843; Amendment Submitted with Request for Continued Examination; Jun. 2, 2009.
Stewart et al., "DICOM image integration into an electronic medical record using thin viewing clients"; Proceedings of the SPIE—The International Society for Optical Engineering, vol. 3339, Feb. 24-26, 1998, pp. 322-328.
U.S. Appl. No. 09/851,745; Response; Jul. 6, 2009.
U.S. Appl. No. 09/851,745; Advisory Action; Jul. 23, 2009.
U.S. Appl. No. 09/851,745; RCE/IDS; Jul. 28, 2009.
U.S. Appl. No. 09/851,745; Office Action; Dec. 10, 2009.
U.S. Appl. No. 09/851,745; Examiner's Interview Summary; Jun. 10, 2010.
U.S. Appl. No. 09/851,745; Response; Jun. 10, 2010.
U.S. Appl. No. 09/851,745; Notice of Allowance; Sep. 24, 2010.
U.S. Appl. No. 09/851,745; Amendment After Allowance; Dec. 23, 2010.
U.S. Appl. No. 10/369,843; Office Action; Sep. 14, 2009.
U.S. Appl. No. 10/369,843; Response; Mar. 15, 2010.
U.S. Appl. No. 10/369,843; Office Action; Jun. 25, 2010.
U.S. Appl. No. 10/369,843; Response; Dec. 23, 2010.
U.S. Appl. No. 10/369,843; Notice of Allowance; Feb. 9, 2011.
Smith, Kevin L.; Statement of Facts in Support of Filing on Behalf of Non-signing Inventor; U.S. Appl. No. 09/170,509; Jan. 19, 1999.
Smith, Kevin L.; Letter to Deborah Jenkins; Oct. 22, 1998.
Smith, Kevin L.; Letter to Deborah Jenkins; Nov. 4, 1998.
Jenkins, Deborah L; Letter to Kevin L. Smith; Nov. 12, 1998.
Smith, Kevin L.; Letter to Deborah Jenkins; Nov. 25, 1998.
Smith, Kevin L.; Letter to Deborah Jenkins; Dec. 17, 1998.
Jenkins, Deborah L.; Letter to Kevin L. Smith; Dec. 21, 1998.
Smith, Kevin L.; Letter to Deborah Jenkins; Dec. 22, 1998.
Jenkins, Deborah L.; Letter to Kevin L. Smith; Dec. 22, 1998.
Jenkins, Deborah L.; Declaration in U.S. Appl. No. 09/170,509; Dec. 24, 1998.
Akers, Wm. Rex; Statement Establishing Proprietary Interest in U.S. Appl. No. 09/170,509; Jan. 19, 1999.
Akers, Wm. Rex; Added Page to Declaration by Person with Sufficient Proprietary Interest U.S. Appl. No. 09/170,509; Jan. 19, 1999.

* cited by examiner

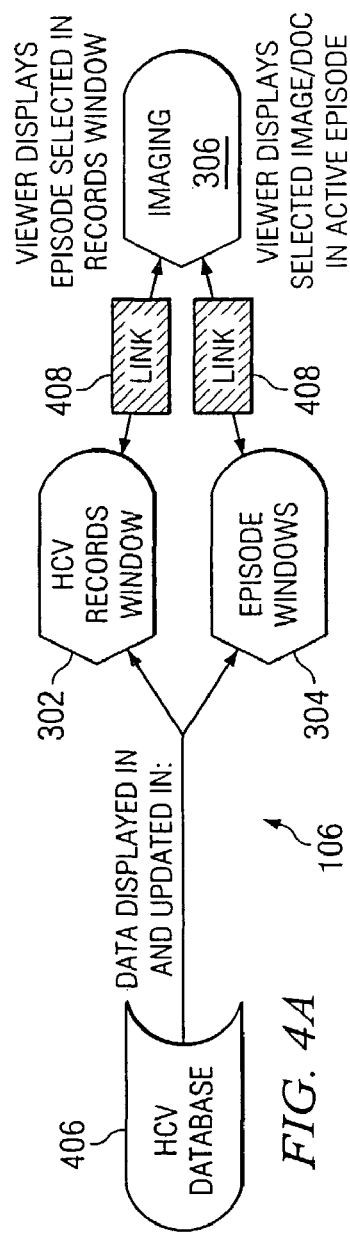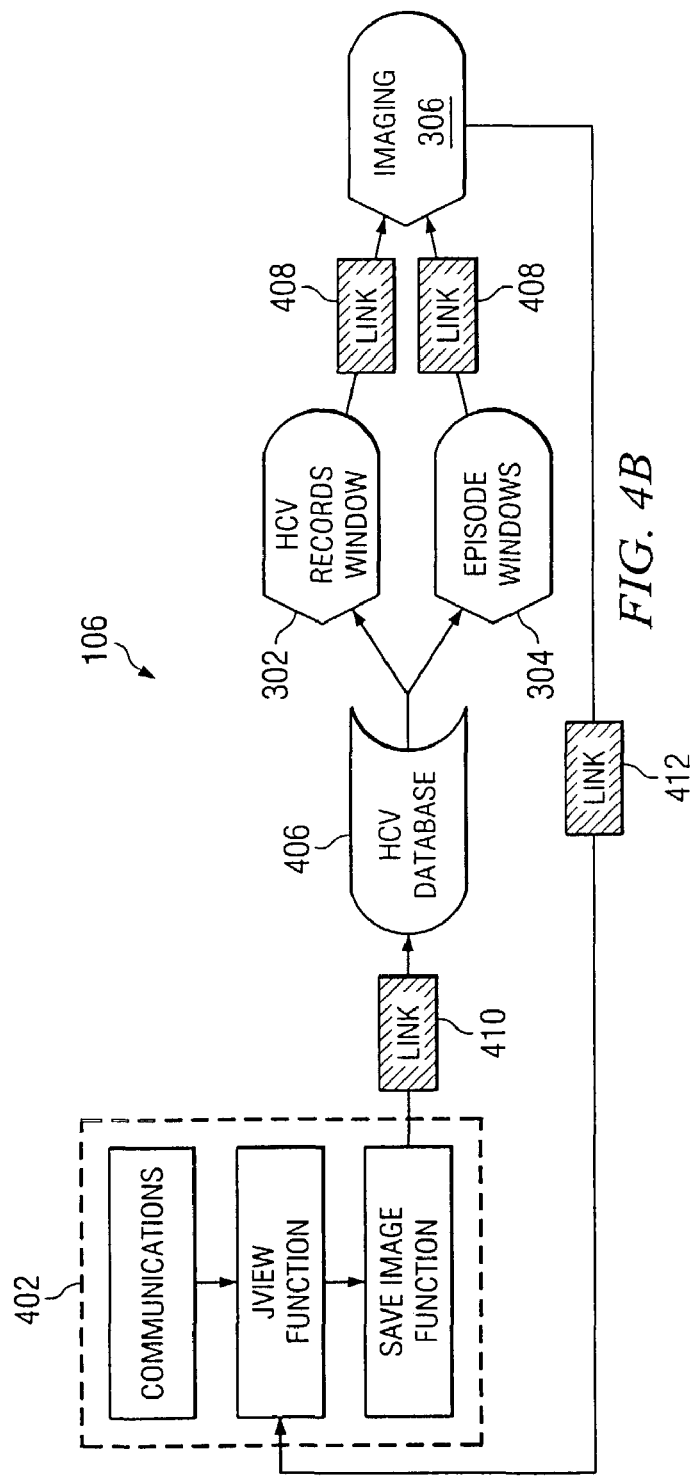
FIG. 4A
FIG. 4B

APPARATUS AND METHOD FOR COMPUTERIZED MULTI-MEDIA DATA ORGANIZATION AND TRANSMISSION

CROSS-REFERENCE TO RELATED APPLICATIONS

This application is a Continuation of the U.S. patent application Ser. No. 09/170,509 filed Oct. 13, 1998 now U.S. Pat. No. 6,597,392, which claims the benefit of U.S. Provisional Application Ser. No. 60/061,761 filed Oct. 14, 1997, which is incorporated herein by reference.

TECHNICAL FIELD

The present invention relates to a computer-implemented diagnostic imaging tool for capturing multi-media data for organization and transmission from a database, and in particular to a telemedicine technique using multi-media data capture, storage, and transmission of episodes-of-care for medical consultation.

BACKGROUND OF THE INVENTION

In remote areas of the world, or with infirm patients unable to travel to hospitals, telecommunications have historically been used to attempt diagnosis over distances. In the beginning, voice conversations were held with physicians in an effort to diagnose a patient over a distance. But the diagnosis was often unreliable because the examining physician was unable to view the patient and their symptoms first-hand, leaving the accuracy of the diagnosis to the capability of the caregiver with the patient to relay the information with sufficient information for a diagnosis.

Improvements had been made with the use of image transfers over telecommunications lines. The images of the affected region—such as ulcers, lesions, or the like—could be electronically transmitted to a physician for review. But this method had limitations due to the inaccuracy of time records to track development of a condition. Also, image files would have haphazard naming conventions that failed to convey any meaning to those unfamiliar with the naming conventions of the primary medical provider. Another limitations of remote patient care devices has been the user acceptance to deploy the technology in the marketplace.

Thus, a need exists for an inexpensive device for capturing multi-media data for organization and transmission from a database that is portable with the medical community. Further, a need exists for a high-definition capture device to provide high-definition images for analysis. Also, a need exists for arranging the high-definition images, with pertinent date-time information, in an orderly manner that is readily accessible by a user.

BRIEF SUMMARY OF THE INVENTION

Accordingly, the present invention provides an apparatus for multi-media data organization and transmission. The apparatus has a computer having a microprocessor, a memory storage, a display for providing information to a user, and an input device. An image-recording device is electrically-coupled to the computer for capturing images for storage in the memory storage of the computer. A database, which has a structure defined in the memory storage, receives and stores a plurality of information relating to an event. A program, being executable by the computer, provides a graphical user interface on the display. The program has an imaging module with document and image capture filing and scanning functions. The graphical user interface receives an input from the input device and from the image-recording device. In a further aspect of the invention, the program has a communications module for transmission of the plurality of information relating to the event to a remote location.

The foregoing has outlined rather broadly the features and technical advantages of the present invention in order that the detailed description of the invention that follows may be better understood. Additional features and advantages of the invention will be described hereinafter which form the subject of the claims of the invention.

BRIEF DESCRIPTION OF THE SEVERAL VIEWS OF THE DRAWING

For a more complete understanding of the present invention, and the advantages thereof, reference is now made to the following descriptions taken in conjunction with the accompanying drawings, in which:

FIGS. 4A-4C are program structure diagrams of the present invention regarding the interconnection of the program modules through connecting links.

DETAILED DESCRIPTION OF THE INVENTION

Figure 1:
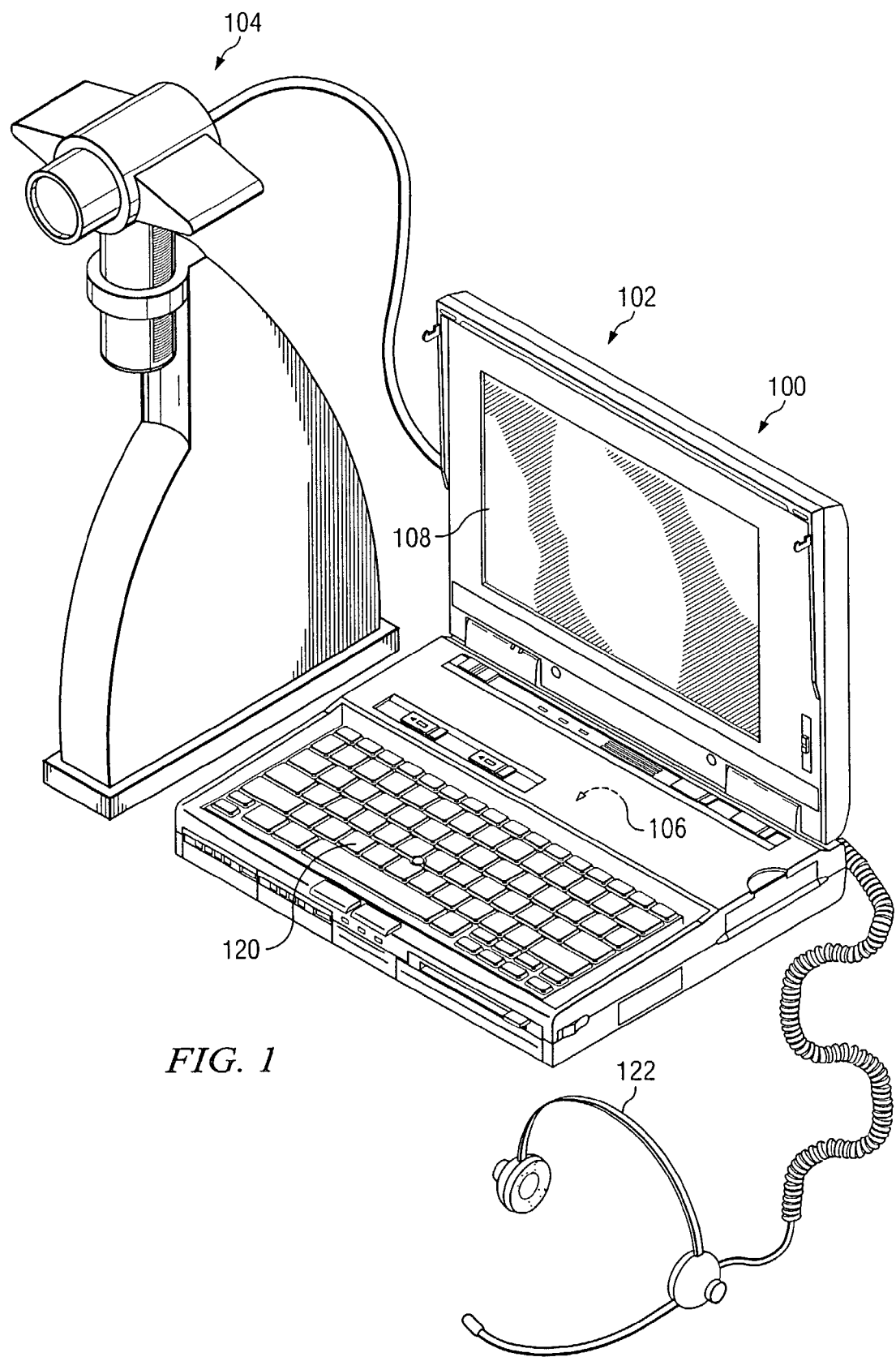
FIG. 1 is an illustration of the capture-and-storage device of the present invention for providing health care access to remote and rural patients with image-assisted diagnosis.

In the following description, numerous specific details are set forth to provide a thorough understanding of the present invention. It should be noted, however, that those skilled in the art are capable of practicing the present invention without such specific details. Referring to the drawings, depicted elements are not necessarily shown to scale, and like or similar elements are designated by the same reference numeral through the several views.

Provided herein is a telemedicine solution to improve homecare and customer service while reducing medical costs by allowing patients to remain at home. It should be noted that although the present invention is described with reference to use in the medical field, the present invention has applications to fields where image-assisted analysis is desired without the need for traveling conventionally required by on-site examination. For example, other conceivable applications would be for mechanical analysis, for peer discussions, or for telecommuting where input is sought from others over a remote distance.

Referring to FIG. 1, the capture-and-storage device 100 of the present invention utilizes existing telephone phone lines to provide health care access to remote and rural patients with image-assisted diagnosis. The ability to use low-level communications lines such as POTS ("Plain Old Telephone System") gives the health care diagnostician greater access to patients. Such communications systems are presently used with conventional MODEM devices that allow the computer to transmit information over standard telephone lines. Nevertheless, as communications technologies advance, such as the widespread implementation of ISDN (Integrated Service Digital Network), other telecommunications technologies can be implemented to allow the transfer of multimedia data.

The capture-and-storage device 100 has a portable laptop computer 102, a digital camera 104, and an executable software program 106, which is installed on, and executed by, the laptop computer 102 to provide image capture, transfer, and database storage. An executable program is understood to be a computer program that is ready to run. The term refers to a compiled program that has been translated into machine code in a format that can be loaded into memory and executed by the microprocessor; however, for interpreted languages, the term can simply refer to source code in the proper format.

The laptop computer 102 preferably has a 5×86 microprocessor operating at about 133 MHZ, a color display screen 18 sufficient to convey adequate information to the user for analysis, and sufficient random-access-memory (RAM) to accommodate the images. A suitable laptop computer is available from Toshiba America Information Systems.

The digital camera 104 has macro focus and low light capabilities. A suitable digital camera is a model Pixera Professional available from Pixera Corporation of Los Gatos, Calif. It should be noted, however, that as technology advances, faster computers with more powerful microprocessor and graphics capability can be used.

The software program 106 loaded into the program memory is executed by the microprocessor of the laptop computer 102 to provide video and audio conferencing capabilities to enable a diagnostician to survey a patient from a remote site. The term "remote" as used herein means not in the immediate vicinity of the computer system 102, the computer system being remotely accessible by another device located in another place (being a room, building, city, state, or country) that is accessible through some type of cable or communications link.

The capture-and-storage device 100 captures high resolution still-images that can also be transmitted to corresponding computer devices connected across the telecommunications path, or transferred using common file transfer techniques associated with computer technology, as is known in the art. These images can be annotated by both parties, and saved or discarded. When saved, the software program 106 saves the images and related patient information in. a patient "episode-of-care" folder for patient history and for retrieval purposes.

In another application—such as with rural health care, homecare, long term care facilities, or the like—the capture-and-storage device 100 can be used for data acquisition. For example, a homecare nurse at a patient residence can connect to a physician through a video conferencing session provided by the software program 106. Both parties can have their cameras in use, or just at the patient site. Once in the care session, the nurse or the physician can capture a still image from the remote camera 104. The captured-image can then be shared between the parties and be mutually annotated by each party to discuss care for a particular symptom. Each party has the capability to save an image or images for their records and end the session.

The saved data images are stored in the device 100 database and electronic file cabinet, along with information on the patient, nurse, physician, service date, and capture date of each image. A memo field is also available for both the nurse and the physician to record additional information. The filed information is "hot synchronized" to keep a united record for the health system. Furthermore, additional scanned information pertinent to the patient can be added to the database record at any time, such as prescriptions image, X-ray images, pathology report images, or the like. The term "image" as used herein, refers to a digital representation of a document or other such information.

A description of the software program 106 follows regarding the integrated software solution for capturing multi-media data for organization and transmission with a database.

Figure 2:
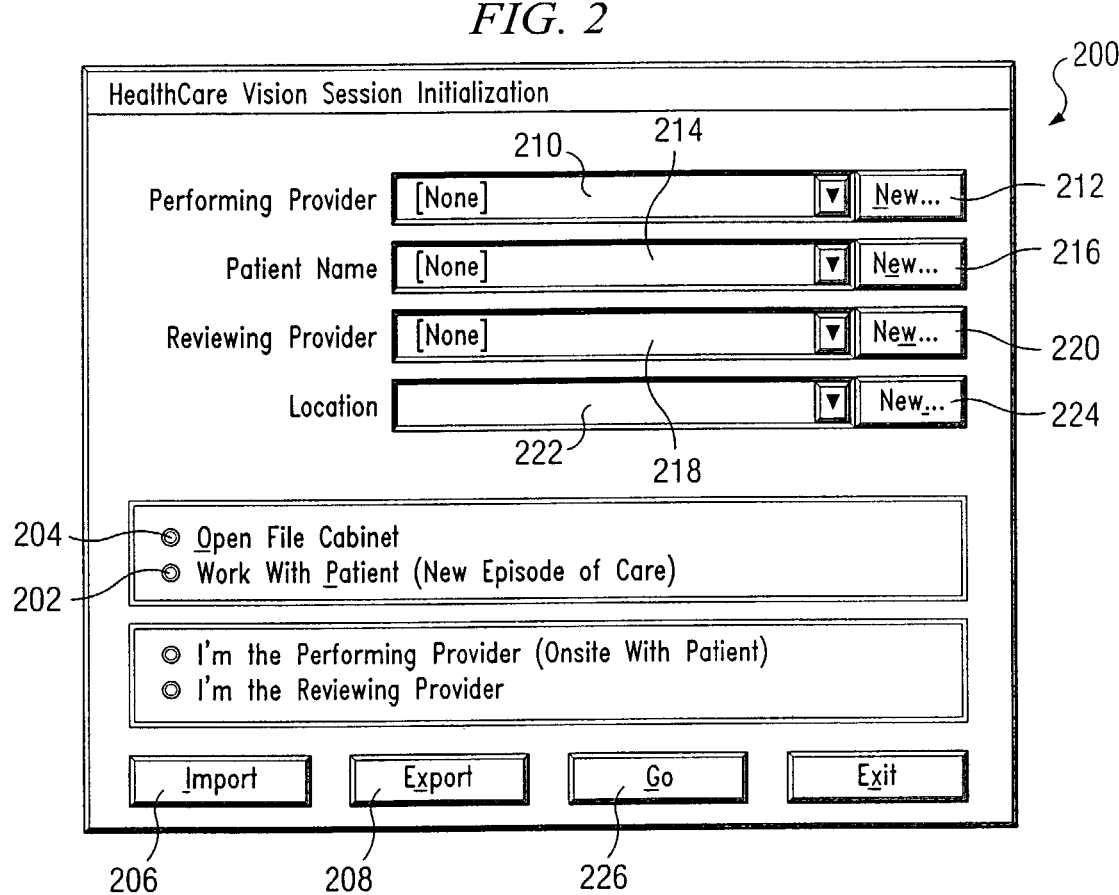
FIG. 2 is an illustration of session initialization window of the present invention.

FIG. 2 shows a session initialization window 200. Upon activation of the device and selection of the software program 106 for execution by the computer 102 (see FIG. 1). The activation of the software program 106 can take place through conventional invocation techniques such as pressing an icon indicating selection of the program or through voice commands via the headset 122. Activating the program 106 loads the database into program memory, and prompts the user to make selections through the session initialization window 200.

Three options are available through the Session Initialization window 200: (1) work with the patient by pressing icon 202; (2) Open_the_File Cabinet function (to look at patient history, make notes, append documents, etc.) by pressing icon 204; or (3) import or export records to or from another device 100 by pressing either icon 206 or icon 208.

With pressing either the icon 202 or icon 204, Work_with_the_Patient function (begin a new episode-of-care), or the Open_the_File_Cabinet functions are selected. If so, then the user selects a Performing Provider (the provider onsite with the patient) for the field 210 from the pick list or adds them by clicking on the "New" button 212, and then selecting a patient name for the field 214 from the pick list or add a Patient by clicking on the "New" button 216. Optionally, a Reviewing Provider (the Provider that will be called) is selected in the field 218 from the pick list or add a Reviewing Provider by clicking on the "New" button 220. Also, as an option a location (the location where the patient is being seen) is selected in the field 222 from the pick list or adds a location by clicking on the "New" button 224.

With this information in place, and the mode selected through the Open_File_Cabinet icon 204 or through the Work_with_Patient icon 202. The "Open File Cabinet" option invokes the data viewing aspects of the device 100 opening the communications and capture functions, discussed later in detail. The "Work with Patient" function invokes a new episode-of-care, which opens both the data aspects of the device 100 by opening the "electronic file cabinet" and the communications and data capture software packages. The execution of the selected option takes place by pressing the "Go" button 226.

Selecting the import icon 206 or the export icon 208 imports or exports records to or from another device 100. The underlying functions are known to those skilled in the art and are not discussed in detail. The "Import" function is available if imported files are stored on the device 100 and have not been imported. Selecting the import icon 206 initiates importing files from a sending device 100. Files received from the transmitting device are merged with files on the receiving system 100. With the export icon 208 selected, the report files to be exported are copied to a temporary Export directory for file transfer, and are then exported from the device 100 according to a specified date range.

With respect to the "Open File Cabinet" mode and the "Work with Patient" mode, the same information is available for review, analysis, and commentary by the reviewing provider. The difference, however, is that additional data acquisition and communications capabilities are made available through the "Work with Patient" mode.

Figure 3:
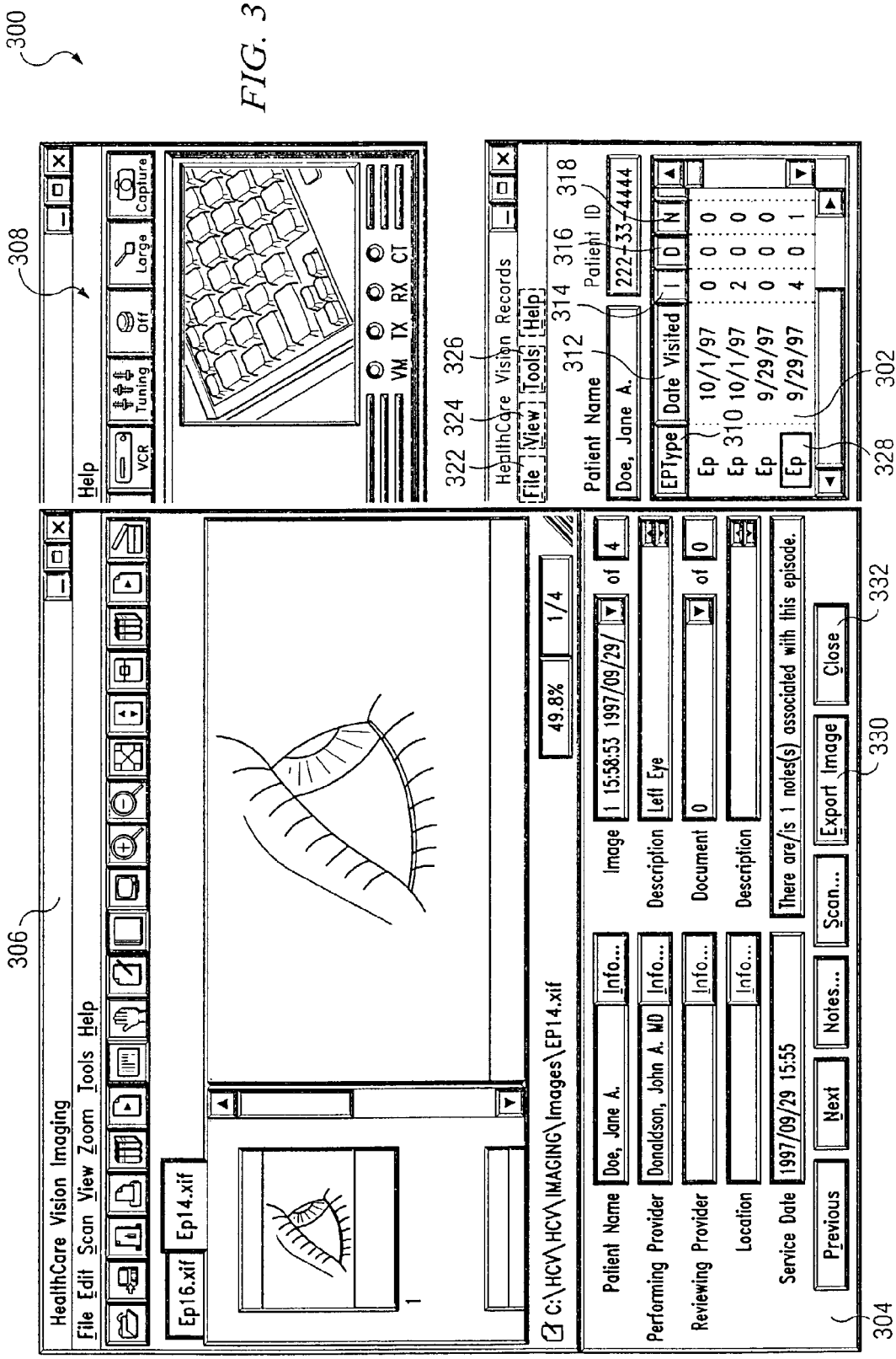
FIG. 3 is an illustration of a Graphical User Interface ("GUI") of the present invention for receiving input and for displaying data.

Referring to FIG. 3, shown is a Graphical User Interface ("GUI") 300 displayed on the screen 18. The GUI 300 is provided by the executable program 106 (see FIG. 1). The configuration shown in FIG. 3 is representative of the appearance of the user interface for the device 100 when in the "Open File Cabinet" mode or the "Work with Patient" mode invoked through the Session Initialization window 200 (see FIG. 2).

If the "Open File Cabinet" mode is chosen, the selected patient history (prior episodes) is displayed in a records window 302. An imaging window 306 displays the image(s) associated with the most recent episode-of-care (in this example, one image from a session on 29 Sep. 1997). In this mode, the prior episodes can be accessed and reviewed, or searches conducted on the database.

If the "Work with Patient" mode is chosen, a new episode-of-care for the selected patient is started. The patient and provider names are "written" into the database with the current date (taken from the internal clock of the computer 102). The GUI 300 displays the records window 302, the episode information window 304, an imaging window 306, and a communications-and-image-capture window 308. The records window 302 displays an overview on the data for the current session, and the previous sessions for the patient, if any. The episode information window 304 displays data for the session that entered through the Session Initialization window 200 (see FIG. 2), and the data is updated as the provider session progresses. The image window 306 is initially blank until an image is captured through the controls of the image capture window 308.

A GUI is a type of display format that enables the user to choose commands, start programs, and view lists of files and the operation by pointing to pictorial representations (icons) and lists of menu items on the screen. Choices can generally be activated either with the keyboard 120 or with a mouse. Graphical user interfaces are used on the Apple Macintosh and by such programs as Microsoft Windows, and the OS/2 Presentation Manager.

Additionally, choices may also be activated using a voice-command software package and associated communications headset 122 to provide voice-activation and voice transcription of notes. Such a feature allows the provider to work with the patient to capture, transmit, and store data images without having to resort to manual keystrokes. A further advantage of voice-command is the user-friendly feature available to users having limited computer skills. A suitable voice-command module is available from Verbex Voice Systems, of Edison, N.J.

In FIG. 3, the GUI 300 shows, in a side-by-side orientation, a records window 302, an episode information window 304, an imaging window 306, and a communications-and-image-capture window 308. These windows are invoked through the selection of modes in the session initialization window 200 (see FIG. 2) discussed above in detail.

The term "window," as used in the applications and graphical interface contexts, is understood to be a portion of the screen that can contain its own document or message. In window-based programs such as GUIs, the screen can be divided into several windows, each of which has its own boundaries and can contain a different document (or another view into the same document). It should be noted that the windows of the GUI 200 can be placed in an overlapped orientation.

The GUI 200 provides a data input/output path to a software database, which in conjunction with the keyboard 120 and the headset 122, and mouse if used, a user can provide multimedia information that is readily accessed and updated through the GUI, including graphical image data captured with the digital camera 104.

A software database is an aggregation of data, which is arranged in a number of records or tables, each of which is constructed of fields (or columns) of a particular type, together with a collection of operations that facilitate searching, sorting, recombination, and similar activities. A suitable database is available under the mark ACCESS® from Microsoft, Inc., of Seattle, Wash.

The software database is the organizational aspect of the device 100. Text and graphical data information, or program indexes, are stored in the database for each session or episode-of-care. The database has a series of tables that allow organization and storage on a per-episode basis. In this manner, a vast amount of useful information is conveyed to a user at one time on which to base diagnosis and treatments, as well as the gathering and storage of such information in a concise location. Up to this time, such availability required consulting with numerous physicians and specialists, as well as culling through numerous files and charts to arrive at a suitable treatment. The software database has the following tables:

| No | Table | Description |
|---|---|---|
| 1 | Docs | This table tracks scanned documents and document folders. All data is entered by the software application except for the optional page title, which is entered by the user in the Episode window 204. |
| 2 | Episode | This is the Master Table, which keeps track of image folders, document folders, notes, patients, providers and location information for each visit. All data is entered by the software application. |
| 3 | Images | Keeps track of saved images and their associated information through the JView window 208. All information is entered by the software application except for the optional image title, which is entered by the user in the Episode window 204. |
| 4 | Location | Contains data storage location information. Data is accessed from the Session Initialization, the records window 202, and the episode information window 204. The dialog box fields are the Location_ID, Type, Description, and Facility. |
| 5 | LocType | A sub-table for the Location Table that codifies location information. Values are preloaded by manufacturer and are based on the ANSI ANSI X12 data dictionary. |
| 6 | Notes | Contains notes, creator of note and time/date information. Notes are entered by the user in the episode window 204. |
| 7 | Patient | Contains the name, address, and demographic information on patients. Data is entered by the user. This table is accessed from the session initialization window, the records window 202, and the episode window 204. The Patient ID number is the database record key, and is the data field used to tie the database to other health care applications. |
| 8 | PatientIDTypes | A sub-table for the Patient table that contains qualifiers to indicate the type or source of the patient ID number. Values are preloaded by the device manufacturer, and are based on the ANSI ASC X12 data dictionary. |
| 9 | Pharmacy | Sub-table of the Patient table |
| 10 | Provider | Contains name, address, and demographic information on all health care providers. Data is entered by the user. This is accessed from the session initialization screen, the records window 202, and the episode window 204. |
| 11 | ProviderCode | A sub-table for the Provider table that contains qualifiers to indicate the type of provider. Values are preloaded by the device manufacturer, and are based on the ANSI ASC X12 data dictionary. |
| 12 | ProviderIDType | A sub-table for the Provider table that contains qualifiers to indicate the type or source of the provider ID number. Values are preloaded by the device manufacturer, and are based on the ANSI ASC X12 data dictionary. |

First details concerning the database structure are provided in Appendix A, which is incorporated herein by reference.

The records window 302 provides several fields for accepting and displaying information. In general, the records window 302 is a nexus of the capture-and-storage device 100 in that the functions associated with the episode information window 304, the imaging window 306, and the communications-and-image-capture window 308 are spawned by selections and actions taken in this window. In this manner, a centralized record containing text, images, annotations can be created that is complete within itself.

The records window 302 has a Type field 310, which shows whether the session was an Episode (created by using Work-with-Patient mode) or a Document folder. A document folder can be attached to a patient file drawer without being associated with a particular episode. The Date_Visited field 312 shows the date of the session. Sessions are organized in the table from most recent to the oldest. The "I" field 314 shows a numerical count of the number of images in the Episode folder for that session. The "D" field 316 shows a numerical count of the number of scanned document pages in the associated document folder that is part of the Episode for that session. The "N" field 318 shows a numerical count of the number of associated notes for the episode. The Loc field 320 has a two character descriptor of the type of facility where the session was performed. This list is shown in Appendix A in the LocType table, IDUser column.

When selected, the File Menu 322 of the records window 302 provides several user options. The menus options are Scan, Print, New_Episode_of_Care, or Search_for_Records.

When the Scan option is selected, the user can select "To Patient File" to scan a document or image to a non-Episode folder that is associated globally to the patient (not ,to a particular Episode). On the other hand, the user can select "To This Episode" to scan a document or image to a Doc folder having the same "x" designator as the Episode and is associated with the current Episode shown in the record window 302. The number of document pages is then displayed in the "D" field 316 of the Episode shown in the record window 302.

When the Print option is selected, the user can print a total record or a data only record. If the user chooses to print Data_and_Images, then each image and each document associated with the selected Episode is printed. The database information sheet that is printed contains: (a) Episode ID; (b) Episode Type; (c) Date/Time Visited; (d) Patient ID; (e) Patient Name; (f) Performing Provider Name; (g) Reviewing Provider Name; and (h) Notes, each with Provider Name and the Date/Time of entry.

Each image in the Episode folder is printed on a separate page with a header that displays "Captured Image x of x from Episode x." Each page in the associated document folder is printed on a separate page with a header the displays "Document x of x from Episode x."

If the user selects the New_$_{Episode}$_of_Care option, then the user is returned to the session initialization window 200 to select new options or to exit the system.

If the user selects the Search_for_Records option, the user is able to key in search terms that are searched for in the database. If a narrower search is desired, search categories can be used, such as providers and patients, a specific episode of care between a specific beginning and end date, or based on a location identifier or location description.

Still referring to FIG. 3, the View Menu 324 is selected to allow a user to view additional information for a selected episode shown in the record window 302. If the "Episode Information" option is selected, the episode information window 304 is spawned. The episode information window 304 is discussed later in detail.

Also, the "Patient Information," "Provider Information," "Location Information" or "Notes" options can be selected from the View Menu 324. Upon selection, a display window is invoked to show the detailed information associated with these tables.

The Tools Menu 326 of the records window 302 allows a user to add new patients, providers or locations to the database. These additions can also be done in the session initialization window 200.

As discussed above, when the "Episode Information" option is selected from the View Menu 324, the episode information window 304. By highlighting a different Episode line with the window cursor 328 in the listing of the records window 302, the information displayed in the episode information window 304 and the imaging window 306 will change accordingly to reflect data stored with respect to that episode.

The episode information window 304 displays database information, and accepts database information. This window is titled "Current Episode" under the Work with Patient mode and is automatically displayed when the application begins. This window is titled "Episode Information" under the Open File Cabinet mode and is opened by choosing the View Episode Information option in the records window 304.

This window functions mainly on buttons and pull-down menus. It has the following data fields:

Patient Name—This shows the name of the selected patient. Pressing the "Info" button next to this field pops-up the Patient screen. The Patient information can also be accessed from the records window 302.

Performing Provider—This shows the name of the Performing Provider for the Episode. Pressing the "Info" button next to this field pops-up the Provider screen. The Provider information can also be accessed from the records window 302.

Reviewing Provider—This shows the name of the Reviewing Provider (if one is active) for the Episode. Pressing the "Info" button next to this field pops-up the Provider screen. The Provider information can also be accessed from the records window 302.

Location—This shows the description of the Location (if one is active) for the Episode. Pressing the "Info . . . " button next to this field pops-up the Location screen. The Location information can also be accessed from the records window 304.

Service Date—Displays the date and type of the Episode. This is taken from the system clock of the computer 102.

Image of x—Displays the number of images for the Episode, with the individual number and date/time stamp in the first box and the total number of images for the Episode in the second box. Using the down arrow displays information on the other images in the folder. Selecting an image by moving the arrow, changes the information in this window and refocuses the image viewed in the imaging module window.

Description—The "Description" box directly beneath the "Image" box displays the title of the currently displayed image. Clicking the mouse in the box allows input of data. This box displays the optional title of the currently selected image.

Document of x—Displays the number of pages in the optional Document folder for the Episode, with the individual number and date/time stamp in the first box and the total number of documents for the Episode in the second box. Using the down arrow displays information on the other documents in the folder. Selecting a document by moving the arrow changes the information in this window and refocuses the document viewed in the imaging window 306.

Description—The "Description" box directly beneath the "Document" box displays the title of the currently displayed document page. Clicking the mouse in the box allows input of data. This box displays the optional title of the currently selected document page.

Notes—The last field on the window shows how many notes are associated with the Episode. Notes are accessed through the "Notes" button or the records window 302.

The image communications functions of the GUI 300 is carried out through the "Export Image" key 330, which selects the current image in the imaging window 306 and sends it to the communications-and-image-capture window 308 for transfer to a connected party. If in the event the communications-and-image-capture window 308 is not active, the window will open and the image will be displayed within.

The "Close" key 332 closes the episode information window 304. If the device 100 is in the "Work with Patient" mode, then the program returns to the session initialization window 200 (see FIG. 2). Otherwise, if the program is in the "Open File Cabinet" mode, the "Close" key 332 simply closes the episode information window 304.

Figure 4C:
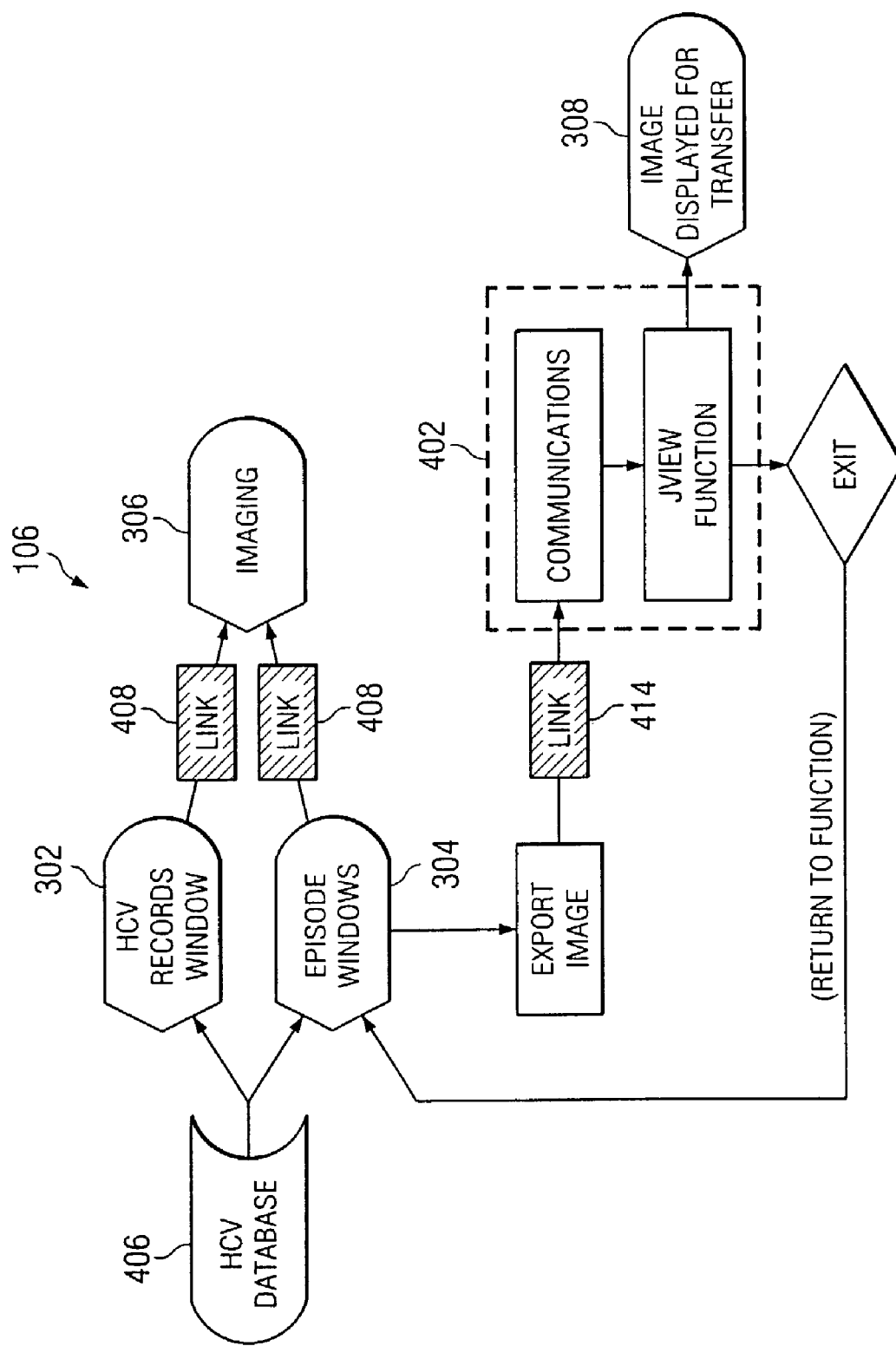

FIGS. 4A through 4C are program structure diagrams regarding the interconnection of the program modules through connecting links. The software program 106 initially referred to with respect to FIG. 1 is an integrated solution that has several program function modules to provide multimedia information formats to a user. The software program 106 has a communications module 402, an imaging module 404, and a database 406, which is discussed in detail above and with respect to Appendix A. Connecting links 408, 410, 412, 414, and 416 respectively interconnect the communications module 402 and imaging module 404, respectively, for integration with the database 406. Such links between the program modules are known to those skilled in the art.

The communications module 402 captures images, can establish a phone connection to a similar device 10, can share images with a similar device 10, and can save images for later recall. A suitable communications module is available under the product name AudioVision from Smith Micro Software of Aliso Viejo, Calif. The AudioVision product provides two-way video and audio communications over the Internet, intranet, or standard POTS lines using standard analog modem connections. The operation of such products is known to those skilled in the art and accordingly, is not discussed in further detail. The communications module is activated when the "Work with Patient" option is selected, invoking the communications-and-image-capture window 308 (see FIG. 3).

The communications module 402 has a JView plug-in function, which is a high resolution image capture, annotate, and store program. The JView function program can capture a 640×480×24 bit true-color image through the digital camera 104 (see FIG. 1), and is linked with connecting link 390, illustrated in Appendix C, Diagram 3, that enables the JView module to pass data to the imaging module 340.

When JView is selected, the high resolution viewer is activated and overlays most of the screen as illustrated in Appendix A, Screen Diagram 15. The communication module 320 can operate with and without an established telecommunications connection between the two parties. If there is a telecommunications connection, then additional features are made available.

Referring to FIG. 4A, the imaging module 404 is an electronic filing cabinet with document and image filing and scanning capabilities. A suitable imaging module is available under the product name ViewWise from WhetStone Technologies of Park City, Utah. The imaging module serves as links 408 between the records window 302 and the episode window 304. The imaging module 404 displays the image/document folder selected in the record window 302, and the selected image or document of the episode information window 304.

Referring to FIG. 4B, when an image is saved through the JView function of the communications-and-image-capture window 308, the link 410 is activated to pass the image and associated information (size, compression ratio, date/time stamp) to the database 406 for storage. The captured image is placed in the episode folder of for the patient and is given a unique identifier for retrieval and identification purposes. If multiple images are saved for an episode, they are all written to the episode folder. The software application 106 automatically gives each data image a unique filename. When JView is exited, the user is prompted whether to save any images that have not already been saved.

The record window 302 is updated to reflect the image was captured in the "I" field 314 (see FIG. 3). The episode information window 304 is similarly updated to display the active image. The program 106 then returns to the communication module 402 to conduct further image processing when called by the user.

During the saving of an image to a patient Episode-of-Care folder, the images are transferred from the communications module 402 to the imaging module 404 (the electronic file cabinet).

As the saved images are imported into the file cabinet, they are converted into a XIF format, with each image being a JPEG file. The typical JPEG compression is set at 75, but the user has the option to alter this. If altered on the communication module 402 side, the connecting link 410 will pass the new value to the image module, and the data image will be saved accordingly. The time/date stamp becomes a permanent part of the image and cannot be removed. The file formats were chosen to maintain the quality of the image and to reduce storage requirements. A 640×480×24 bit image is 921,600 bytes while a typical compressed JPEG for storage is from about 30,000 to about 50,000 bytes.

Referring to FIG. 4C, shown is the program structure for opening previously saved data images for analysis or retransmission. Again through the JView plug-in function of the communications module 402, link 414 allows the export of a stored image from the database 406 to the communications module 402. When the retrieved image is in the possession of the communications module 402, the image can be transmitted to a connected reviewer. This is done with the connecting link 395 on the Current Episode window that "exports" the currently displayed image from the imaging window 306, invokes the JView function, and displays the image in the communications-and-image-capture window 308. The user then selects "Transmit" to send the image to a reviewer. The image is opened with the same attributes it had when it was saved. The time/date stamp is displayed and the quality is set to the value it had when originally saved.

The user can opt to review a previous episode before taking new images. For example, this might be important if they want to capture a wound from the same angle as it was taken during the last patient visit. To select a previous episode, they can either highlight the episode in "Date Visited" field 312 in the records window 302 to a previous episode, or older sessions can be viewed accordingly. Once a previous episode is selected, the imaging window 306 displays the images in that folder, and the episode information window 304 displays information about that episode (see FIG. 3).

Although the invention has been described with reference to a specific embodiment, these descriptions are not meant to be construed in a limiting sense. Various modifications of the disclosed embodiments, as well as alternative embodiments of the invention will become apparent to persons skilled in the art upon reference to the description of the invention. It is therefore contemplated that the claims will cover any such modifications or embodiments that fall within the true scope and spirit of the invention.

What is claimed is:

1. An apparatus for multi-media data organization and transmission of information relating to the provision of service on-site, the apparatus comprising:
   an on-site computer having a microprocessor, a memory storage, a display for providing information to an on-site service provider, and an input device for receiving information and commands from the on-site service provider;
   a remote computer having a microprocessor and a memory storage;
   a display for providing information to a remote service provider, and an input device for receiving information and commands from a remote service provider;
   a database defined in said memory storage of said on-site computer for storing a plurality of on-site episode records, each on-site episode record for storing one or more images relating to an event and a plurality of fields of information relating to the event, said database comprising provision for annotations of said images;
   a database defined in said memory storage of said remote computer for storing a plurality of remote episode records, each remote episode record for storing one or more images relating to an event and a plurality of fields of information relating to the event, said database comprising provision for annotations of said images;
   an imaging device operatively coupled to said memory storage of said on-site computer for capturing images for storage in said on-site episode records;
   a program executable by said on-site computer, said program providing a graphical user interface on said display of said on-site computer, said program having an imaging module with document and image capture filing and scanning functions, said graphical user interface accepting an input from said input device of said on-site computer to control said program;
   a communications module of the on-site computer configured to modify at least a portion of an on-site episode record in the plurality of on-site episode records in accordance with a modification to at least a portion of a remote episode record in the plurality of remote episode records; and
   a communications module of the remote computer configured to modify at least the portion of the remote episode record in accordance with a modification to at least the portion of the on-site episode record.

2. The apparatus of claim 1, wherein said program has a data synchronizer for making at least some of the data contents of the database defined in said memory storage of said on-site computer and at least some of the data contents of the database defined in said memory storage of said remote computer the same.

3. The apparatus of claim 1, wherein said input device of the on-site computer is a computer keyboard.

4. The apparatus of claim 1, wherein said input device of the on-site computer is a voice-command program executed by said on-site computer, said voice-command program receiving input from hardware operatively-coupled to said on-site computer.

5. The apparatus of claim 1, wherein each event is an episode-of-care in which health care services are provided.

6. The apparatus of claim 1, wherein said imaging device is a digital camera.

7. The apparatus of claim 1, wherein the at least one on-site episode record comprises a graphic image having a date/time stamp.

8. The apparatus of claim 7, wherein said graphic image is in XIF format.

9. The apparatus of claim 1, wherein said imaging module is an electronic filing cabinet program.

10. An apparatus for multi-media data organization and transmission of information relating to the provision of service on-site, the apparatus comprising:
    an on-site computer having a microprocessor, a memory storage, a display for information that will be provided to a remote service provider, and an input device for entering information and commands from the remote service provider;
    a remote computer having a microprocessor and a memory storage;
    a data structure defined in said memory storage of said on-site computer for storing one or more on-site episode records, each on-site episode record for storing one or more images relating to an event and a plurality of fields of information relating to the event, said data structure comprising provision for associating said information with said images;
    a data structure defined in said memory storage of said remote computer for storing one or more remote episode records, each remote episode record for storing one or more images relating to an event and a plurality of fields of information relating to the event;
    an imaging device operatively coupled to said memory storage of said on-site computer for generating images for storage in said on-site episode record;
    a program executable by said on-site computer, said program providing a user interface of said on-site computer, said program having an imaging module with image generation functions, and said user interface accepting an input to control said program;
    a communications module of the on-site computer configured to modify at least a portion of an on-site episode record in the one or more on-site episode records in accordance with a modification to at least a portion of a remote episode record in the one or more of remote episode records; and
    a communications module of the remote computer configured to modify at least the portion of the remote episode record in accordance with a modification to at least the portion of the on-site episode record.

11. The apparatus of claim 10, wherein said program has a data synchronizer for making at least some of the data contents of the database defined in said memory storage of said on-site computer and at least some of the data contents of the database defined in said memory storage of said remote computer the same.

12. The apparatus of claim 10, wherein said on-site episode record comprises a plurality of fields of information comprising one or more of the group comprising an on-site computer identifier, patient identification data, time data, date data, and data used to generate diagnostic data.

13. The apparatus of claim 10, wherein said input device of the on-site computer is a voice-command program executed by said on-site computer.

14. The apparatus of claim 10, wherein each event is an episode-of-care in which health care services are provided.

15. The apparatus of claim 10, wherein said an imaging device is a digital camera.

16. The apparatus of claim 10, wherein the on-site episode record comprises a date/time stamp.

17. The apparatus of claim 10, wherein said communications module is responsive to commands received from the remote service provider.

18. The apparatus of claim 10, wherein said imaging module is an electronic filing cabinet program.

19. An apparatus for multi-media data organization and transmission of information relating to the provision of service, the apparatus comprising:
   an on-site computer having a microprocessor, a memory storage, a display for providing information to an on-site operator, and an input device for receiving information and commands from the on-site operator;
   a remote computer having a microprocessor and a memory storage;
   a display for providing information to a remote operator, and an input device for receiving information and commands from a remote service provider;
   a database defined in said memory storage of said on-site computer for storing a plurality of on-site episode records and a plurality of on-site images, each on-site episode record for storing a plurality of fields of information relating to an event, each on-site image associated with an on-site episode record, said database comprising provision for annotations of said images;
   a database defined in said memory storage of said remote computer for storing a plurality of remote episode records and a plurality of remote images, each remote episode record for storing a plurality of fields of information relating to an event, said database comprising provision for annotations of said images;
   an imaging device operatively coupled to said memory storage of said on-site computer for capturing images for storage in said database defined in said memory storage of said on-site computer;
   a program executable by said on-site computer, said program providing a graphical user interface on said display of said on-site computer, said program having an imaging module with document and image capture filing and scanning functions, said graphical user interface accepting an input from said input device of said on-site computer, or from said remote service provider to control said program;
   a communications module of the on-site computer configured to modify at least a portion of an on-site episode record in the plurality of on-site episode records in accordance with a modification to at least a portion of a remote episode record in the plurality of remote episode records; and
   a communications module of the remote computer configured to modify at least the portion of the remote episode record in accordance with a modification to at least the portion of the on-site episode record.

20. The apparatus of claim 19, wherein said program has a data synchronizer for making at least some of the data contents of the database defined in said memory storage of said on-site computer and at least some of the data contents of the database defined in said memory storage of said remote computer the same.

21. The apparatus of claim 19, wherein said input device of the on-site computer is a computer keyboard.

22. The apparatus of claim 19, wherein said input device of the on-site computer is a voice-command program executed by said on-site computer, said voice-command program receiving input from hardware operatively-coupled to said on-site computer.

23. The apparatus of claim 19, wherein said event is an episode-of-care in which health care services are provided.

24. The apparatus of claim 19, wherein said imaging device is a digital camera.

25. The apparatus of claim 19, wherein the at least one on-site image comprises a graphic image having a date/time stamp.

26. The apparatus of claim 25, wherein said graphic image is in XIF format.

27. The apparatus of claim 19, wherein said imaging module is an electronic filing cabinet program.

28. An apparatus for multi-media data organization and transmission of information relating to the provision of service, the apparatus comprising:
   an on-site computer having a microprocessor, a memory storage, a display for information that will be provided to a remote operator, and an input device for entering information and commands from the remote operator;
   a remote computer having a microprocessor and a memory storage;
   a data structure defined in said memory storage of said on-site computer for storing
      one or more on-site episode records comprising an on-site episode record, the on-site episode record for storing a plurality of fields of information relating to an event; and
      one or more on-site images associated with the on-site episode record;
   a data structure defined in said memory storage of said remote computer for storing:
      one or more remote episode records comprising a remote episode record, the remote episode record for storing a plurality of fields of information relating to an event; and
      one or more remote images associated with the remote episode record;
   an imaging device operatively coupled to said memory storage of said on-site computer for generating images for storage in said data structure defined in said memory storage of said on-site computer and associated with said on-site episode record;
   a program executable by said on-site computer, said program providing a user interface of said on-site computer, said program having an imaging module with image generation functions, and said user interface accepting an input to control said program;
   a communications module of the on-site computer configured to annotate an on-site image in the one or more on-site images in accordance with an annotation to a remote image in the one or more remote images; and
   a communications module of the remote computer configured to annotate the remote image in accordance with an annotation to the on-site image.

29. The apparatus of claim 28, wherein said program has a data synchronizer for making at least some of the data contents of the database defined in said memory storage of said on-site computer and at least some of the data contents of the database defined in said memory storage of said remote computer the same.

30. The apparatus of claim 28, wherein said on-site episode record comprises a plurality of fields of information comprising one or more of the group comprising an on-site computer identifier, patient identification data, time data, date data, and data used to generate diagnostic data.

31. The apparatus of claim 28, wherein said input device of the on-site computer is a voice-command program executed by said on-site computer.

32. The apparatus of claim 28, wherein each event is an episode-of-care in which health care services are provided.

33. The apparatus of claim 28, wherein said an imaging device is a digital camera.

34. The apparatus of claim 28, wherein said information is a date/time stamp.

35. The apparatus of claim 28, wherein said communications module is responsive to commands received from the remote operator.

36. The apparatus of claim 28, wherein said imaging module is an electronic filing cabinet program.

37. An apparatus for multi-media data organization and transmission of information relating to the provision of service on-site, the apparatus comprising:
 an on-site computer;
 a remote computer;
 a data structure accessible to the on-site computer storing one or more on-site episode records, each on-site episode record for storing one or more images relating to an event and a plurality of fields of information relating to the event;
 a data structure accessible to the remote computer storing one or more remote episode records, each remote episode record for storing one or more images relating to an event and a plurality of fields of information relating to the event;
 an imaging device operatively coupled to a memory storage of the on-site computer and configured to generate images for storage in the on-site episode record;
 a program executable by the on-site computer, the program providing a user interface of said on-site computer, the program having an imaging module with image generation functions, and the user interface accepting an input to control said program;
 a communications module of the on-site computer configured to modify at least a portion of an on-site episode record in the one or more on-site episode records in accordance with a modification to at least a portion of a remote episode record in the one or more remote episode records; and
 a communications module of the remote computer configured to modify at least the portion of the remote episode record in accordance with a modification to at least the portion of the on-site episode record.

38. The apparatus of claim 37, further comprising a data synchronizer configured to make at least some of the data contents of the data structure accessible to the remote computer and at least some of the data contents of the data structure accessible to the on-site computer the same.

39. The apparatus of claim 37, wherein the data structure accessible to the on-site computer is stored in a memory storage of the on-site computer.

40. The apparatus of claim 37, wherein the data structure accessible to the remote computer is stored in a memory storage of the remote computer.

41. The apparatus of claim 37, wherein the on-site computer is configured to cause the imaging device to generate an image in response to input from a person at the location of the on-site computer.

42. The apparatus of claim 37, wherein the remote computer is configured to cause the imaging device to generate an image in response to input from a person at the location of the remote computer.

43. The apparatus of claim 37, wherein the imaging device is a digital camera.

44. The apparatus of claim 37, wherein each episode record further comprises an episode record for storing an annotation to one or more images relating to an event.

45. The apparatus of claim 37, wherein each episode record further comprises an episode record for storing a memo about the episode record.

46. The apparatus of claim 37, wherein each event is an episode of health care services.

47. A method for multi-media data organization and transmission of information relating to the provision of service on-site, the method comprising:
 creating an episode record having a unique identifier at an on-site computer;
 capturing an image related to the episode record;
 storing the image in the episode record at the on-site computer;
 transmitting the episode record to a remote computer;
 modifying at least a portion of the episode record at the on-site computer in accordance with a modification to at least a portion of the episode record at the remote computer; and
 modifying at least the portion of the episode record at the remote computer in accordance with a modification to at least the portion of the episode record at the on-site computer.

48. The method of claim 47, wherein the data in the episode record at the remote computer is stored in a memory storage of the on-site computer.

49. The method of claim 47, wherein the data in the episode record at the remote computer is stored in a memory storage of the remote computer.

50. The method of claim 47, wherein the image is captured in response to input from a person at the location of the on-site computer.

51. The method of claim 47, wherein the image is captured in response to input from a person at the location of the remote computer.

52. The method of claim 47, wherein the imaging device is a digital camera.

53. The method of claim 47, wherein the modification comprises an annotation to the image.

54. The method of claim 47, wherein the modification comprises a memo about the episode record.

55. The method of claim 47, wherein the event is an episode of health care services.

56. A computer program product, stored on a non-transitory computer-readable medium, for multi-media data organization and transmission of information relating to the provision of service on-site, the computer program product comprising:
 computer code for creating an episode record having a unique identifier at an on-site computer computer code for capturing an image related to the episode record;
 computer code for storing the image in the episode record at the on-site computer;
 computer code for transmitting the episode record to a remote computer;
 computer code for modifying at least a portion of the episode record at the on-site computer in accordance with a modification to at least a portion of the episode record at the remote computer; and computer code for modifying at least the portion of the episode record at the remote computer in accordance with a modification to at least the portion of the episode record at the on-site computer.

57. The computer program product of claim 56, wherein the data in the episode record at the on-site computer is stored in a memory storage of the on-site computer.

58. The computer program product of claim 56, wherein the data in the episode record at the remote computer is stored in a memory storage of the remote computer.

59. The computer program product of claim 56, wherein the image is captured in response to input from a person at the location of the on-site computer.

60. The computer program product of claim 56, wherein the image is captured in response to input from a person at the location of the remote computer.

61. The computer program product of claim 56, wherein the imaging device is a digital camera.

62. The computer program product of claim 56, wherein the modification comprises an annotation to the image.

63. The computer program product of claim 56, wherein the modification comprises a memo about the episode record.

64. The computer program product of claim 56, wherein the event is an episode of health care services.

\* \* \* \* \*